United States Patent [19]

Pellico et al.

[11] Patent Number: 4,537,764

[45] Date of Patent: Aug. 27, 1985

[54] STABILIZED ENZYMATIC DENTIFRICE CONTAINING B-D-GLUCOSE AND GLUCOSE OXIDASE

[75] Inventors: Michael A. Pellico; Robert E. Montgomery, both of Los Angeles, Calif.

[73] Assignee: Laclede Professional Products, Inc., Gardena, Calif.

[21] Appl. No.: 501,383

[22] Filed: Jun. 6, 1983

Related U.S. Application Data

[63] Continuation-in-part of Ser. No. 292,633, Aug. 13, 1981, abandoned.

[51] Int. Cl.³ .................. A61K 7/28; A61K 37/48; A61K 37/50
[52] U.S. Cl. .................. 424/50; 424/49; 424/94; 435/188; 435/190
[58] Field of Search .......... 424/50, 94; 435/188, 435/190

[56] References Cited

U.S. PATENT DOCUMENTS

| | | | |
|---|---|---|---|
| 85,166 | 12/1868 | Colburn | 424/58 |
| 152,098 | 6/1874 | Forster | 424/58 |
| 396,192 | 1/1889 | Clark | 424/58 |
| 1,169,998 | 2/1916 | Rhodes | 424/49 |
| 1,275,275 | 8/1918 | Levinson | 424/49 |
| 1,386,252 | 8/1921 | Green | 424/50 |
| 1,460,179 | 6/1923 | Ruthrauff | 424/58 |
| 1,492,299 | 4/1924 | Kyle et al. | 424/58 |
| 1,536,305 | 5/1925 | Nitaroy | 424/58 |
| 1,739,586 | 12/1929 | Gerngross et al. | 424/129 |
| 1,740,543 | 12/1929 | Gerngross et al. | 424/129 |
| 1,943,467 | 1/1934 | Bley | 424/50 |
| 3,574,824 | 4/1971 | Echeandia et al. | 424/50 |
| 3,855,142 | 12/1974 | Pader et al. | 424/50 |
| 3,860,484 | 1/1975 | O'Malley | 435/190 |
| 4,012,839 | 3/1977 | Hill | 424/129 |
| 4,082,841 | 4/1978 | Pader | 424/50 |
| 4,150,113 | 4/1979 | Hoogendoorn et al. | 424/50 |
| 4,178,362 | 12/1979 | Hoogendoorn et al. | 424/50 |
| 4,250,254 | 2/1981 | Modrovich | 435/190 |
| 4,269,822 | 5/1981 | Pellico et al. | 424/50 |
| 4,271,264 | 6/1981 | Modrovich | 435/190 |
| 4,310,625 | 1/1982 | Modrovich | 435/190 |
| 4,320,116 | 3/1982 | Bjorck | 424/129 |
| 4,331,761 | 5/1982 | Dawson et al. | 435/188 |
| 4,349,533 | 9/1982 | Dent et al. | 424/52 |
| 4,366,243 | 12/1982 | Rupchock et al. | 435/188 |
| 4,372,874 | 2/1983 | Modrovich | 435/188 |
| 4,394,449 | 7/1983 | Modrovich | 435/188 |

FOREIGN PATENT DOCUMENTS

| | | | |
|---|---|---|---|
| 749329 | 12/1966 | Canada | 435/188 |
| 4675M | 1/1967 | France | 424/50 |
| 2132980 | 11/1972 | France | 424/50 |

OTHER PUBLICATIONS

C. A. 37#1467(4)#2036(8)#3789(3)#4421(1)(1943) 38#137(6)(1944) 39#5261(1)(1945).
C. A. 40#6546(6)(1946) 41#2165c(1947) 42#4636A#4625D (1948) 43#3857(1) (1949).
C. A. 44#4055(1)(1950).
C. A. 32#721(2)(1938) 44#6573i (1950) 46#3852(1)(1952) 50#7918f (1956).
Dixon et al "Enzymes" Academic Press (1958) N.Y., pp. 184-185, 202-203, 284-287, 344-345, 354-355, 438-439, 682-683, 688-689, 706-707.
USPTO Translation of FR 4675M (1/67) (11 pages), and FR 2 132980 (11/72), (8 pages).

*Primary Examiner*—Shep K. Rose
*Attorney, Agent, or Firm*—Donald Diamond

[57] ABSTRACT

An enzymatic dentifrice is provided which contains an enzyme system comprising Beta-D-glucose and glucose oxidase for producing hydrogen peroxide upon oral application of the dentifrice. The enzymatic dentifrice is stabilized against the production of hydrogen peroxide prior to oral application of the dentifrice by limiting any water in the dentifrice to an amount not more than about 10 wt. % based on the weight of the dentifrice.

10 Claims, No Drawings

STABILIZED ENZYMATIC DENTIFRICE CONTAINING B-D-GLUCOSE AND GLUCOSE OXIDASE

CROSS-REFERENCE TO RELATED APPLICATION

This application is a continuation-in-part of U.S. patent application Ser. No. 292,633, filed Aug. 13, 1981, now abandoned, and entitled Di-Enzymatic Dentifrice.

BACKGROUND OF THE INVENTION

This invention relates to dentifrice compositions and, more particularly, to antiseptic dentifrice compositions containing Beta-D-glucose and glucose oxidase for producing hydrogen peroxide in situ during oral application of the dentifrice.

Dentifrices, in powder, paste, cream and liquid forms, are used for both cosmetic and therapeutic purposes. Consistent with these purposes, dentifrices are formulated to contain active ingredients such as cleansing and polishing materials, as well as various antibacterial and anticaries agents for use as aids in the prevention of tooth decay.

It is generally understood in the dental art that certain kinds of tooth decay are initiated by acid etching of the tooth enamel with the source of the acid being a metabolite resulting from bacterial and enzymatic action on food particles in the oral cavity. It is generally accepted that plaque—which is a soft accumulation on the tooth surfaces consisting of an organized structure of microorganisms, proteinaceous and carbohydrate substances, epithelial cells, and food debris—is a contributory factor in the development of various pathological conditions of the teeth and soft tissue of the oral cavity. It has been suggested that the saccharolytic organisms of the oral cavity, which are associates with the plaque cause decalcification beneath the plaque matrix through metabolic activity which results in the accumulation and localized concentration of organic acids. The etching and decalcification of the enamel may continue until the pulp chamber of the tooth is reached.

A wide variety of materials have been considered for use as decay-preventative agents in dentifrice compositions. Some of the substances which have been so considered include para-aminobenzoic acid, a combination of urea and urease to produce ammonia during oral application of the dentifrice, chlorophyll, perflourinated long chain organic compounds, complex iodine, penicillin, benzohydroxamic acid, and glucose oxidase to produce hydrogen peroxide during oral application of the dentifrice.

U.S. Pat. No. 2,526,614 (Butterfield, 1950) discloses the incorporation into a dentifrice of an enzyme system comprising urea and urease which produces ammonia in the presence of moisture that is encountered during oral application of the dentifrice. The patentee reports that the action of the ammonia together with residual urea is bacterocidal to acidogenic organisms and antienzymatic to the production of lactic acid by such organisms. In addition, it is pointed out that the action of ammonia produced from this enzyme system dissolves mucin plaques.

U.S. Pat. No. 3,427,380 (Kirkland, 1969) discloses that oral organisms produce a capsular material which is a factor in holding plaque together and allowing its further growth and that the oral application of a dentifrice containing para-aminobezoic acid inhibits capsule formation by such organisms and thereby retards the development of dental plaque without inhibiting the growth of these organisms.

U.S. Pat. No. 3,137,634 (Schiraldi, 1964) discloses that the oral application of a dentifrice composition containing, for example, potassium copper chlorophyllin, dicalcium phosphate and tetrasodium pyrophosphate is useful in the treatment of gum diseases such as periodontal disorders like gingivitis, pyorrhea and trench mouth and, in addition, reduces undesirable breath odors.

U.S. Pat. No. 3,227,618 (Dunellen, 1966), in the background portion of the specification, recites that it has been disclosed that treatment of tooth enamel with a mixture of stannous flouride, hydrogen peroxide and insoluble sodium metaphosphate increases the enamel hardness as described in The Journal of the American Dental Association, May, 1950, Vol. 40, pg. 513–519.

U.S. Pat. No. 3,574,824 (Echeandia, et al., 1971) discloses an anhydrous toothpaste base to which can be added enzymes identified as proteases, polysaccharidases, and lipases for the purpose of retarding plaque formation through the breakdown of ingested proteins, carbohydrates and fats.

Merck Index, 9th Edition, 1976, at page 633, discloses that hydrogen peroxide solution 3% contains 2.5–3.5 wt. % of hydrogen peroxide which is equivalent to 8–12 volumes of oxygen, and that this solution is a topical anti-infective which is useful in pharmaceutical preparations such as mouthwashes, dentifrices, and sanitary lotions.

U.S. Pat. No. 4,150,113, (Hoogendoorn et al., 1979) discloses an enzymatic dentifrice containing glucose oxidase which acts on glucose present in saliva and tooth plaque to produce hydrogen peroxide. The patentees, after noting that oral bacteria effect glycolysis of food products containing sugars through bacterial enzyme systems having SH-groups, point out that lactoperoxidase, which is present in saliva, provides the means for transferring oxygen from hydrogen peroxide to the oral bacteria resulting in the oxidation of the SH-containing enzymes into inactive disulfide enzymes. It is further disclosed that the dentifrice may be formulated with potassium thiocyanate.

Hoogendoorn, et al., Carries Research, 11:77–84, 1977 disclose that the hypothiocyanate ion is the bacterial inhibitor formed by the system containing lactoperoxidase, thiocyanate and hydrogen peroxide.

U.S. Pat. No. 4,269,822 (Pellico et al., 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

U.S. Pat. No. 2,891,868 (Heggie, 1959) discloses that chewing gum which is formulated with an oxygen sensitive flavoring agent can be protected against oxidative deterioration of the flavoring agent by incorporating into the formulation an enzyme system containing glucose, glucose oxidase and catalase, and that this protection is effective in the presence of bound water only and does not require free water.

Commercial glucose oxidase which also contains catalase is promoted to the food and beverage industry as an agent for protecting their susceptible packaged products against deterioration in the presence of oxygen and/or glucose by effecting an enzymatic in situ reaction which results in the consumption of oxygen and glucose with the ultimate end product of the enzymatic reaction being gluconic acid.

The effectiveness of a glucose oxidase dentifrice (U.S. Pat. No. 4,150,133) as a bacterial inhibitor through an enzymatic reaction upon oral application is dependent, to a significant extent, upon the subsisting oral concentration of glucose at the time of the oral application of the dentifrice. The concentration of glucose supplied by saliva varies as a direct function of its biological production and salivary flow. Thus, when salivary flow is at a diminished level either as a natural event or as an event arising out of certain types of medical treatment, the oral concentration of glucose will be correspondingly reduced which, in turn, is a limiting factor in the oral production of hydrogen peroxide, a precursor of the hypothiocyanate bacterial inhibitor. It is generally reported in the literature that the mean salivary glucose concentration in adults is about 0.1 millimoles per liter (or about 0.0001 millimoles per gram). Accordingly, it would be advantageous to provide a package and shelf stable, enzymatic dentifrice containing glucose oxidase and Beta-D-glucose at suitable concentration levels for generating reasonably predictable amounts of hydrogen peroxide upon oral application of the dentifrice and thereby overcome the uncertainties associated with the use of a glucose oxidase dentifrice that relies upon salivary glucose as the source of the substrate for the hydrogen peroxide generating reaction.

SUMMARY OF THE INVENTION

In accordance with one aspect of this invention, there is provided an enzymatic dentifrice comprising, per gram of dentifrice, from about 0.015 to about 0.6 millimoles of Beta-D-glucose and from about 0.5 to about 500 International Units of glucose oxidase for producing hydrogen peroxide upon oral application of the dentifrice, and limiting any water present in the dentifrice to an amount not more than about 10 wt. % based on the dentifrice weight to stabilize the dentifrice against the production of hydrogen peroxide prior to oral application of the dentifrice.

In accordance with a second aspect of this invention, there is provided a method for cleaning an oral dental surface which comprises treating the dental surface with an enzymatic dentifrice comprising, per gram of dentifrice, from about 0.015 to about 0.6 millimoles of Beta-D-glucose and from about 0.5 to about 500 International Units of glucose oxidase for producing hydrogen peroxide upon oral application of the dentifrice, and limiting any water present in the dentifrice to an amount not more than about 10 wt. % based on the dentifrice weight to stabilize the dentifrice against the production of hydrogen peroxide prior to oral application of the dentifrice.

DETAILED DESCRIPTION

The enzymatic dentifrice of this invention comprises an enzyme system containing an oxidizable substrate, Beta-D-glucose, and an oxidoreductase enzyme specific to such substrate, glucose oxidase, for producing hydrogen peroxide upon oral application of the dentifrice, with the chemical environment of the oral cavity providing the source of the additional reactants (oxygen, water) to effect the enzymatic reaction.

Glucose oxidase is characterized in the literature as a glycoprotein containing two molecules of flavine-adenine dinucleotide which has a molecular weight of approximately 150,000, an isoelectric point at pH 4.2 and an optimum pH at 5.5 with a broad pH range from 4 through 7.

Glucose oxidase is generally present in the enzymatic dentifrice in an amount from about 0.5 to about 500 International Units (hereinafter sometimes abbreviated as IU) per gram of dentifrice, with an intermediate range being from about 1.0 to about 100 IU per gram of dentifrice, and a preferred range being from about 5.0 to about 50 IU per gram of dentifrice. The term International Unit(s) identifies that amount of enzyme that will effect catalysis of 1.0 micromole of substrate per minute at pH 7.0 and 25° C. Glucose oxidase is supplied in dry or liquid form with the label specifying the concentration in International Units on a per gram or per milliliter basis, as appropriate.

D-Glucose exists in two modifications, Alpha and Beta. Ordinary glucose is primarily Alpha-D-glucose. Beta-D-glucose containing a minor amount of Alpha-D-glucose is available from specialty suppliers. Since glucose oxidase is specific to Beta-D-glucose for effecting the enzymatic reaction that produces hydrogen peroxide, it is, therefore, significantly advantageous to use a glucose composition that is predominantly the Beta form in order to minimize the amount of glucose which is added to the dentifrice and maximize the efficiency of the enzymatic reaction.

Beta-D-Glucose is generally present in the enzymatic dentifrice in an amount from about 0.015 to about 0.6 millimoles per gram of dentifrice, with an intermediate range being from about 0.05 to about 0.5 millimoles per gram of dentifrice, and a preferred range being from about 0.1 to about 0.2 millimoles per gram of dentifrice. The term millimoles identifies that quantity in grams corresponding to the molecular weight divided by one thousand.

Since water not only promotes but is also a reactant in the oxidation/reduction reaction of this invention, the use of water in formulating the enzymatic dentifrice compositions should be at a relatively low concentration level in order to impart maximum stability and shelf life to the compositions. For this purpose, it has been found to be essential to limit any water present in the dentifrice to an amount not more than about 10 wt. %. In view of this water limitation, a non-aqueous fluid carrier is advantageously employed in the toothpaste formulation so as to provide the formulation with pressure responsive flow characteristics. Any suitable non-aqueous fluid may be used for this purpose. Organic fluid carriers, such as glycerine or propylene glycol provide a stable toothpaste environment for the enzyme systems of this invention. The non-aqueous fluid carrier is generally present in the dentifrice composition in an amount from about 30 to about 60 wt. % and, preferably, in an amount from about 45 to about 55 wt. %.

Where the products of the activated enzyme system include a weak organic acid, it is advantageous to formulate the dentifrice with a buffering agent to neutralize the organic acid. A suitable buffering agent is sodium bicarbonate which can be present in the dentifrice in an amount up to about 6 wt. % as, for example, in an amount from about 4 to about 6 wt. %.

Dentifrices, especially toothpaste, are perferred oral compositions for the purpose of this invention. Dentifrice compositions typically contain an abrasive polishing material and a surfactant as well as flavoring, sweetening and coloring agents. Toothpaste usually also contains humectants and thickeners.

Any abrasive polishing material which does not excessively abrade dentin and is compatible with glucose oxidase can be used in the compositions of this invention. These include, for example, calcium carbonate, calcium pyrophosphate, dicalcium phosphate, zirconium oxide and aluminum oxide. The abrasive polishing material is usually present in toothpaste in an amount from about 20 to about 60 wt. %.

The surfactants which can be used are those which yield substantial levels of foam and which are otherwise acceptable for use in the oral cavity and compatible with glucose oxidase. Nonionic surfactants are preferred because they have been found to be most compatible with glucose oxidase. The surfactants can be employed at concentration levels ranging from about 0.5 to about 5.0 wt. %.

The enzymatic dentifrice, in the form of a toothpaste, can be prepared in any suitable manner as, for example, by blending the dry ingredients into the liquid ingredients, with agitation, until a smooth mixture is obtained. The addition of any surfactant to the mixture should take place as the last step in order to minimize foaming of the batch. Also, blending should be carried out under moderate conditions so as to avoid any impairment of the enzyme.

EXAMPLE 1

The following formulations illustrate varying ingredients and concentration levels which can be used in the preparation of the enzymatic dentifrices of this invention. The concentration of B-D-glucose in the Examples is also set forth in millimoles on the basis of one (1) gram of dentifrice.

| 1A | |
|---|---|
| Composition | weight, grams |
| Glycerine (99%) | 50 |
| Calcium Pyrophosphate | 40 |
| Sodium bicarbonate | 5 |
| Color | 0.5 |
| Flavor | 0.5 |
| Beta-D-glucose (0.03 millimoles) | 0.5 |
| Glucose oxidase (100,000 IU/gm) | 0.1 (10,000 IU) |
| Triton X-100 (nonionic surfactant) | 0.4 |
| Water | 3 |

| 1B | |
|---|---|
| Composition | weight, grams |
| Glycerine (99%) | 85 |
| Syloid 244FP (silica thickener) | 10 |
| Glucose oxidase (100,000 IU/gm) | 0.05 (5,000 IU) |
| Beta-D-glucose (0.06 millimoles) | 1 |
| Color | 0.5 |
| Flavor | 0.5 |
| Water | 2.95 |

| 1C | |
|---|---|
| Composition | weight, grams |
| Propylene glycol | 85 |
| Syloid 244FP (silica thickener) | 10 |
| Glucose oxidase (100,000 IU/gm) | 0.02 |
| Beta-D-glucose (0.09 millimoles) | 1.5 |
| Pluronic F87 (nonionic surfactant) | 2.0 |

| 1C -continued | |
|---|---|
| Composition | weight, grams |
| Color | 0.5 |
| Flavor | 0.5 |
| Water | 0.48 |

| 1D | |
|---|---|
| Composition | weight, grams |
| Glycerine (99%) | 42 |
| Dicalcium phosphate | 6 |
| Titanium dioxide | 2 |
| Calcium pyrophosphate | 25 |
| Silcron G-910 (silica thickener) | 13 |
| Glucose oxidase (100,000 IU/gm) | 0.4 (40,000 IU) |
| Beta-D-glucose (0.36 millimoles) | 6 |
| Color | 0.5 |
| Flavor | 0.5 |
| Water | 4.6 |

| 1E | |
|---|---|
| Composition | weight, grams |
| Propylene glycol | 40 |
| Glycerine (99%) | 35 |
| Polyethylene glycol 400 | 10 |
| Syloid 244FP (silica thickener) | 10 |
| Glucose oxidase (100,000 IU/gm) | 0.025 (2500 IU) |
| Beta-D-glucose (0.18 millimoles) | 3 |
| Color | 0.5 |
| Flavor | 0.5 |
| Water | 0.975 |

EXAMPLE 2

This example illustrates an enzymatic dentifrice containing commercial glucose as the source of Beta-D-glucose. The commerical glucose in this example is a dry, free-flowing powder that contains approximately 95% of the Alpha anomer and approximately 5% of the Beta anomer and which is distributed by Corn Products Corporation under the designation Cerelose 2502 USP. Syloid 244FP is the designation for a food grade amorphous silica thickener. Cocoamidopropyl betaine is an amphoteric surfactant.

| Composition | weight (gms) |
|---|---|
| Glycerine 99% USP | 65.48 |
| Syloid 244FP | 15.00 |
| Cerelose 2502 USP (0.06 mM B—D-glucose) | 18.00 |
| Cocoamidopropyl betaine | 1.00 |
| Methyl Salicylate | 0.50 |
| Glucose Oxidase (100,000 IU/gm) | 0.02 |
| | 100.00 |

EXAMPLE 3

U.S. Pat. No. 4,150,113 (hereinafter Hoogendoorn) discloses an enzymatic dentifrice containing glucose oxidase which acts on glucose present in saliva and tooth plaque to produce hydrogen peroxide. An accelerated storage stability study was undertaken to determine the quantity of exudate produced by (A) Hoogendoorn Example II, (B) Hoogendoorn Example II formulated with glucose, and (C) the invention claimed herein.

The procedure employed in the storage stability study included the following steps: Mixing the ingredients and passing the resulting mixture through a 3 roll mill; placing a 50 gram portion of each mixture in the open end of a threadedly capped toothpaste tube which was then crimped at its open end; placing the tubes in a constant temperature water bath at 24° C. for one hour with the caps removed; replacing the caps and placing the water bath and immersed tubes in an oven maintained at 60° C. for 24 hours; removing the water bath and tubes from the oven and maintaining the water bath and tubes at 24° C. for 2 hours and while the tubes are in the bath, removing the caps, waiting 15 minutes, removing the exudate from the tube and weighing the exudate.

The formulations of the toothpaste compositions evaluated in the comparative study were as follows:

| Composition | wt. % (50 g samples) Hoogendoorn Ex. 2 A | Hoogendoorn Ex. 2/glucose B | This Invention C |
|---|---|---|---|
| Calcium carbonate | 50 | 45 | 44 |
| Tricalcium phosphate | 5 | 5 | 5 |
| Sorbitol (70% solution) | 10 | 10 | — |
| Glycerol | 20 | 20 | 40 |
| Tragacanth | 2 | 2 | 3 |
| Aromatic substances | 0.8 | 0.8 | 0.8 |
| Glucose oxidase (0.5 U/g) | | | |
| Dextranase (4 U/g) | | | |
| p-Amino benzoic acid/ PAB-esters | 0.9 | 0.9 | 0.9 |
| Glucose (0.03 millimoles) | — | 5 | 5 |
| Distilled water | 11.3 | 11.3 | 3.3 |
| (Total Water) | (14.3) | (14.3) | (6.3) |
| Exudate, grams | 0.015 | 0.242 | 0.062 |
| Exudate, wt. % | 0.03 | 0.48 | 0.12 |

The storage stability study showed that the addition of glucose to Example II of Hoogendoorn (Run B) resulted in a toothpaste product having an exudate or extrusion factor of 0.48% which represents a 16-fold or 1,600% increase over the 0.03% extrusion factor of Example II without glucose (Run A) and indicates that the addition of glucose effects an in situ reaction resulting in significant and substantial package instability.

The storage stability study showed that the claimed invention (Run C) had a 0.12% extrusion factor which represents a four-fold or 400% improvement in package stability over Example II of Hoogendoorn with glucose.

EXAMPLE 4

The following examples show stabilized enzymatic dentifrice compositions containing glucose oxidase and Beta-D-glucose and which have been further formulated with a second enzyme system containing lactoperoxidase and thiocyanate so as to be self contained with respect to the production of the hypothiocyanate bacterial inhibitor upon oral application of the dentifrice. The term "Maypon" used in the examples is the trademark for a potassium coco condensate of hydrolyzed animal protein having a molecular weight between 750 and 1,500 and supplied as an aqueous solution containing 34 to 40% solids. The term "Super-Pro" used in the examples, is the trademark for an aqueous solution of sorbitol and triethanolamine condensate of hydrolyzed animal having a molecular weight between 750 and 1,500 with the solution having a solids content from 62–70%. The term "Silcron G-910" used in the examples is the trademark for a polishing agent comprising a micron-sized hydrated silica gel.

| 4A Composition | weight, grams |
|---|---|
| Glycerine (99%) | 50 |
| Calcium pyrophosphate | 40 |
| Sodium bicarbonate | 5 |
| Water | 1.5 |
| Super-Pro | 2 |
| Glucose oxidase (100,000 IU/g) | 0.1 (10,000 IU) |
| Beta-D-glucose (0.03 millimoles) | 0.5 |
| Lactoperoxidase (100,000 IU/g) | 0.002 (200 IU) |
| Sodium thiocyanate | 0.04 |
| Color | 0.5 |
| Flavor | 0.5 |

| 4B Composition | weight, grams |
|---|---|
| Glycerine (99%) | 46 |
| Titanium dioxide | 2 |
| Silcron G-910 | 40 |
| Water | 2 |
| Maypon | 2 |
| Glucose oxidase (100,000 IU/g) | 0.05 (5,000 IU) |
| Beta-D-glucose (0.06 millimoles) | 1 |
| Lactoperoxidase (100,000 IU/g) | 0.01 (1,000 IU) |
| Potassium thiocyanate | 0.005 |
| Color | 0.5 |
| Flavor | 0.5 |

| 4C Composition | weight, grams |
|---|---|
| Propylene glycol | 48 |
| Dicalcium phosphate | 45 |
| Water | 3.5 |
| Super-Pro | 2 |
| Glucose oxidase (100,000 IU/g) | 0.0008 (80 IU) |
| Beta-D-glucose (0.03 millimoles) | 0.5 |
| Lactoperoxidase (100,000 IU/g) | 0.005 (500 IU) |
| Sodium thiocyanate | 0.01 |
| Color | 0.5 |
| Flavor | 0.5 |

| 4D Composition | weight, grams |
|---|---|
| Glycerine (99%) | 50 |
| Calcium pyrophosphate | 40 |
| Dicalcium phosphate | 5 |
| Water | 2 |
| Glucose oxidase (100,000 IU/g) | 0.05 (5,000 IU) |
| Beta-D-glucose (0.06 millimoles) | 1 |
| Choline oxidase (100,000 IU/g) | 0.02 (2,000 IU) |
| Choline | 1 |
| Lactoperoxidase (100,000 IU/g) | 0.008 (800 IU) |
| Potassium thiocyanate | 0.009 |
| Color | 0.5 |
| Flavor | 0.5 |

| 4E Composition | weight, grams |
|---|---|
| Glycerine (99%) | 42 |
| Dicalcium phosphate | 6 |
| Titanium dioxide | 2 |
| Silcron G-910 | 38 |
| Water | 5 |
| Glucose oxidase (100,000 IU/g) | 0.4 (40,000 IU) |

-continued

4E

| Composition | weight, grams |
| --- | --- |
| Beta-D-glucose (0.3 millimoles) | 6 |
| Lactoperoxidase (100,000 IU/g) | 0.001 (100 IU) |
| Sodium thiocyanate | 0.01 |
| Color | 0.5 |
| Flavor | 0.5 |

4F

| Composition | weight, grams |
| --- | --- |
| Glycerine (99%) | 42 |
| Dicalcium phoshate | 6 |
| Titanium dioxide | 2 |
| Silcron G-910 | 38 |
| Water | 5 |
| Glucose oxidase (100,000 IU/g) | 0.02 (2,000 IU) |
| Beta-D-glucose (0.06 millimoles) | 1 |
| Lactoperoxidase (100,000 IU/g) | 0.001 (100 IU) |
| Sodium thiocyanate | 0.01 |
| Color | 0.5 |
| Flavor | 0.5 |

4G

| Composition | weight, grams |
| --- | --- |
| Glycerine (99%) | 50 |
| Titanium dioxide | 2 |
| Silcron G-910 | 40 |
| Water | 2 |
| Super-Pro | 2 |
| Glucose oxidase (100,000 IU/g) | 0.02 (2,000 IU) |
| Beta-D-glucose (0.12 millimoles) | 2 |
| Lactoperoxidase (100,000 IU/g) | 0.01 (1,000 IU) |
| Sodium thiocyanate | 0.01 |
| Color | 0.5 |
| Flavor | 0.5 |

4H

| Composition | weight, grams |
| --- | --- |
| Propylene glycol | 44 |
| Sodium bicarbonate | 5 |
| Silcron G-910 | 40 |
| Water | 6.4 |
| Super-Pro | 2 |
| Glucose oxidase (100,000 IU/g) | 0.025 (2,500 IU) |
| Beta-D-glucose (0.09 millimoles) | 1.5 |
| Lactoperoxidase (100,000 IU/g) | 0.006 (600 IU) |
| Potassium thiocyanate | 0.005 |
| Color | 0.5 |
| Flavor | 0.5 |
| N—acetyl glucosamine | 0.15 |

4I

| Composition | weight, grams |
| --- | --- |
| Propylene glycol | 48 |
| Sodium bicarbonate | 5 |
| Silcron G-910 | 40 |
| Water | 2.4 |
| Super-Pro | 2 |
| Glucose oxidase (100,000 IU/g) | 0.025 (2,500 IU) |
| Beta-D-glucose (0.09 millimoles) | 1.5 |
| Lactoperoxidase (100,000 IU/g) | 0.0005 (50 IU) |
| Potassium thiocyanate | 0.005 |
| Color | 0.5 |
| Flavor | 0.5 |
| Glucosamine | 0.1 |

4J

| Composition | weight, grams |
| --- | --- |
| Glycerine (99%) | 47 |
| Sodium bicarbonate | 5 |
| Silcron G-910 | 40 |
| Water | 3.5 |
| Super-Pro | 2 |
| Glucose oxidase (100,000 IU/g) | 0.04 (4,000 IU) |
| Beta-D-glucose (0.09 millimoles) | 1.5 |
| Lactoperoxidase (100,000 IU/g) | 0.012 (1,200 IU) |
| Sodium thiocyanate | 0.05 |
| Color | 0.5 |
| Flavor | 0.5 |
| Glucosamine | 0.012 |
| N—acetyl glucosamine | 0.01 |

In view of the foregoing description and examples, it will become apparent to those of ordinary skill in the art that equivalent modifications thereof may be made without departing from the spirit and scope of this invention.

What which is claimed is:

1. An enzymatic dentifrice comprising, per gram of dentifrice, from about 0.015 to about 0.6 millimoles of Beta-D-glucose and from about 0.5 to about 500 International Units of glucose oxidase for producing hydrogen peroxide upon oral application of said dentifrice, and limiting any water present in the dentifrice to an amount not more than about 10 wt. % based on the dentifrice weight to stabilize the dentifrice against the production of hydrogen peroxide prior to oral application of the dentifrice.

2. The dentifrice of claim 1 wherein the Beta-D-glucose is present in an amount from about 0.05 to about 0.5 millimoles per gram of dentifrice.

3. The dentifrice of claim 1 wherein Beta-D-glucose is present in an amount from about 0.1 to about 0.2 millimoles per gram of dentifrice.

4. The dentifrice of claim 1 wherein glucose oxidase is present in an amount from about 1.0 to about 100 International Units per gram of dentifrice.

5. The dentifrice of claim 1 wherein glucose oxidase is present in an amount from about 5.0 to about 50 International Units per gram of dentifrice.

6. A method for cleaning an oral dental surface which comprises treating the dental surface with an enzymatic dentifrice containing, per gram of dentifrice, from about 0.015 to about 0.6 millimoles of Beta-D-glucose and from about 0.5 to about 500 International Units of glucose oxidase for producing hydrogen peroxide upon oral application of said dentifrice, and limiting any water present in the dentifrice to an amount not more than about 10 wt. % based on the dentifrice weight to stablize the dentifrice against the production of hydrogen peroxide prior to oral application of the dentifrice.

7. The method of claim 6 wherein the Beta-D-glucose is present in an amount from about 0.05 to about 0.5 millimoles per gram of dentifrice.

8. The method of claim 6 wherein the Beta-D-glucose is present in an amount from about 0.1 to about 0.2 millimoles per gram of dentifrice.

9. The method of claim 6 wherein glucose oxidase is present in an amount from about 1.0 to about 100 International Units per gram of dentifrice.

10. The method of claim 6 wherein glucose oxidase is present in an amount from about 5.0 to about 50 International Units per gram of dentifrice.

* * * * *

UNITED STATES PATENT AND TRADEMARK OFFICE
CERTIFICATE OF CORRECTION

PATENT NO. : 4,537,764

DATED : August 27, 1985

INVENTOR(S) : Michael A. Pellico, et al

It is certified that error appears in the above-identified patent and that said Letters Patent is hereby corrected as shown below:

On the title page Item (63) and Column 1, line 10, delete "now abandoned".

Signed and Sealed this

Twenty-fourth Day of December 1985

[SEAL]

Attest:

DONALD J. QUIGG

Attesting Officer

Commissioner of Patents and Trademarks